United States Patent
Anand

(10) Patent No.: US 11,471,098 B2
(45) Date of Patent: Oct. 18, 2022

(54) MONITORING THE EFFECTS OF THERAPEUTICS ON THE BRAIN VIA GENE EXPRESSION AND BRAIN IMAGING

(71) Applicant: THE CLEVELAND CLINIC FOUNDATION, Cleveland, OH (US)

(72) Inventor: Amit Anand, Pepper Pike, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 229 days.

(21) Appl. No.: 16/749,025

(22) Filed: Jan. 22, 2020

(65) Prior Publication Data

US 2020/0155062 A1    May 21, 2020

Related U.S. Application Data

(63) Continuation-in-part of application No. 16/413,896, filed on May 16, 2019, now Pat. No. 10,890,639.
(Continued)

(51) Int. Cl.
*A61B 5/05* (2021.01)
*A61B 5/00* (2006.01)
(Continued)

(52) U.S. Cl.
CPC .......... *A61B 5/4848* (2013.01); *A61B 5/0042* (2013.01); *A61B 5/055* (2013.01); *C12Q 1/6883* (2013.01); *C12Q 2600/158* (2013.01)

(58) Field of Classification Search
CPC . A61B 5/055; A61B 2090/374; A61B 5/0035; A61B 6/032; A61B 6/037
(Continued)

(56) References Cited

U.S. PATENT DOCUMENTS

| 7,723,023 B2 * | 5/2010 | Sealfon | C12Q 1/6883 435/6.14 |
| 2003/0054443 A1 * | 3/2003 | Ruben | C07K 14/47 435/69.1 |

(Continued)

OTHER PUBLICATIONS

Anand, Amit, et al. "Activity and connectivity of brain mood regulating circuit in depression: a functional magnetic resonance study." Biological psychiatry 57.10 (2005): 1079-1088.
(Continued)

*Primary Examiner* — Walter L Lindsay, Jr.
*Assistant Examiner* — Frederick Wenderoth
(74) *Attorney, Agent, or Firm* — Tarolli, Sundheim, Covell & Tummino LLP

(57) ABSTRACT

Systems and methods are provided for monitoring the effects of therapeutics on the brain. Brains of first and second sets of patients are imaged and a gene expression is measured at a first time to provide a first set of images and a first set of gene expression transcripts. A therapeutic is administered to the first set of patients after the first time. The brains of the patients are imaged and the gene expression of the patients is measured at a second time, after the therapeutic is administered, to provide a second set of images and a second set of gene expression transcripts. A change in the brain is determined for the patients from the sets of images. A set of
(Continued)

changes in the gene expression that are correlated with the changes in the brain are determined from the change in the brain and the sets of gene expression transcripts.

20 Claims, 6 Drawing Sheets

Related U.S. Application Data

(60) Provisional application No. 62/672,246, filed on May 16, 2018.

(51) Int. Cl.
*C12Q 1/6883* (2018.01)
*A61B 5/055* (2006.01)

(58) Field of Classification Search
USPC .......................................................... 600/411
See application file for complete search history.

(56) References Cited

U.S. PATENT DOCUMENTS

| | | | |
|---|---|---|---|
| 2006/0074290 A1* | 4/2006 | Chen .................... | G06T 7/0012 600/407 |
| 2008/0241839 A1* | 10/2008 | Potkin .................. | C12Q 1/6881 435/6.16 |

OTHER PUBLICATIONS

Anand, Amit, et al. "Antidepressant effect on connectivity of the mood-regulating circuit: an FMRI study." Neuropsychopharmacology 30.7 (2005): 1334-1344.

Anand, Amit, et al. "Effects of lithium monotherapy for bipolar disorder on gene expression in peripheral lymphocytes." Molecular neuropsychiatry 2.3 (2016): 115-123.

Spielberg, Jeffrey M., et al. "Resting state brain network disturbances related to hypomania and depression in medication-free bipolar disorder." Neuropsychopharmacology 41.13 (2016): 3016-3024.

Hariri, Ahmad R., et al. "Brain-derived neurotrophic factor val66met polymorphism affects human memory-related hippocampal activity and predicts memory performance." Journal of Neuroscience 23 17 (2003): 6690-6694.

Ho, Beng-Choon, et al. "Cognitive and MRI Brain Morphometric Correlates of Brain-Derived Neurotrophic Factor Val66Met Gene Polymorphism in Schizophrenia and Healthy Volunteers." Archives of general psychiatry 63.7 (2006): 731.

Pearlson, Godfrey D., Vince D. Calhoun, and Jingyu Liu. "An introductory review of parallel independent component analysis (p-ICA) and a guide to applying p-ICA to genetic data and imaging phenotypes to identify disease-associated biological pathways and systems in common complex disorders." Frontiers in genetics 6 (2015): 276.

* cited by examiner

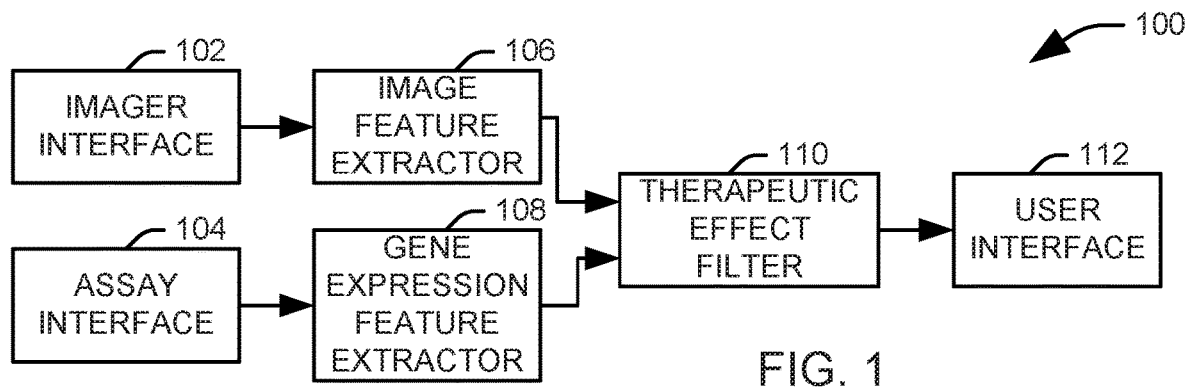
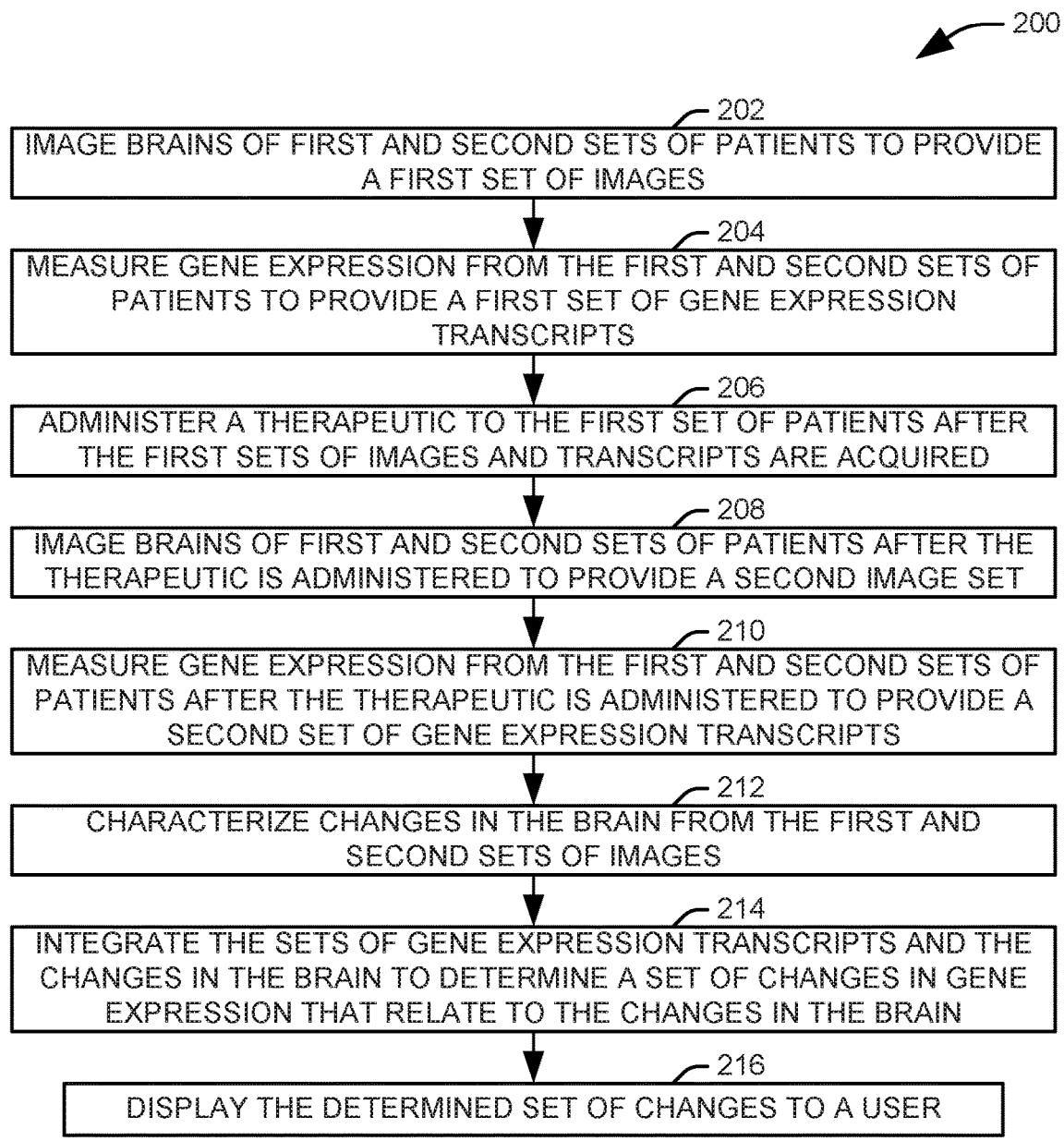

MONITORING THE EFFECTS OF THERAPEUTICS ON THE BRAIN VIA GENE EXPRESSION AND BRAIN IMAGING

RELATED APPLICATIONS

This application is a continuation-in-part of U.S. patent Ser. No. 16/413,896, filed May 16, 2019, which, in turn, claims priority to U.S. Provisional Patent Application Ser. No. 62/672,246 filed May 16, 2018. The entirety each of these applications is hereby incorporated by reference.

TECHNICAL FIELD

This disclosure relates to medical therapeutics and diagnostics and, more particularly, to monitoring the effects of therapeutics on the brain via imaging of the brain and measurement of gene expression in other parts of the body.

BACKGROUND OF THE INVENTION

Psychotropic medications have contributed greatly to the quality of life for patients suffering from neurological and psychiatric disorders. For example, lithium has consistently been shown to decrease suicides as well as overall mortality in subjects who take it. Unfortunately, the specific molecular effects of various therapeutics have cannot easily be evaluated, limiting their significance for clinical treatment and efficacy. Pharmacological effects of drugs acting on the brain cannot be measured directly in living humans, as brain tissue cannot be obtained through a biopsy, and suitable animal models are not available for most neuropsychiatric illnesses. This has impeded methods to monitor the effects of existing therapeutics and the development of new medications with similar efficacy and specificity.

SUMMARY OF THE INVENTION

In accordance with one aspect of the present invention, a method is provided. The brains of each of a first set of patients and a second set of patients are imaged at a first time to provide a first set of images. A gene expression is measured in one of blood cells and tissue stem cells of each of the first set of patients and the second set of patients at the first time to provide a first set of gene expression transcripts. A therapeutic is administered to the first set of patients at a second time that is after the first time. The brains of each of the first set of patients and the second set of patients are imaged at a third time that is after the second time to provide a second set of images. The gene expression of each of the first set of patients and the second set of patients is measured at the third time to provide a second set of gene expression transcripts. A change in one of the structure, function, and chemistry of the brain is determined for each of the first set of patients and the second set of patients from the first set of images and the second set of images. A set of changes in the gene expression that are related to changes in the structure, function or chemistry of the brain are determined from the change in the one of the structure, function, and chemistry of the brain for each of the first set of patients and the second set of patients, the first set of gene expression transcripts, and the second set of gene expression transcripts.

In accordance with another aspect of the present invention, a system includes a processor and a non-transitory computer readable medium that stores executable instructions. The executable instructions include an imager interface that receives a first set of images representing brains of each of a first set of patients and a second set of patients at a first time and a second set of images representing the brains of the first set of patients and the second set of patients at a second time to provide a second set of images. An assay interface receives a first set of gene expression transcripts measuring a gene expression of each of the first set of patients and the second set of patients at the first time and a second set of gene expression transcripts measuring a gene expression of each of the first set of patients and the second set of patients at the second time. An image feature extractor determines, from the first set of images and the second set of images, a set of image features representing a functional, structural, or chemical change in the brain for each patient. A gene expression feature extractor determines, from the first set of gene expression transcripts and the second set of gene expression transcripts, a set of gene expression features representing a change in the gene expression for each patient. A therapeutic effect filter determines, from the set of image features and the set of gene expression features, a set of changes in the gene expression that are related to changes in the connectivity of the brain.

In accordance with yet another aspect of the present invention, the brains of each of a first set of patients and a second set of patients are imaged at a first time to provide a first set of images. A peripheral lymphocyte gene expression of each of the first set of patients and the second set of patients is measured at the first time to provide a first set of gene expression transcripts. The brains of each of the first set of patients and the second set of patients are measured at a second time to provide a second set of images. The peripheral lymphocyte gene expression of each of the first set of patients and the second set of patients is measured at the second time to provide a second set of gene expression transcripts. A therapeutic is administered to the first set of patients at a third time between the first time and the second time. A change in the connectivity of the brain for each of the first set of patients and the second set of patients is determined from the first set of images and the second set of images. A set of changes in the peripheral lymphocyte gene expression that are related to changes in the connectivity of the brain is determined from the change in the connectivity of the brain for each of the first set of patients and the second set of patients, the first set of gene expression transcripts, and the second set of gene expression transcripts.

BRIEF DESCRIPTION OF THE DRAWINGS

FIG. 1 illustrates a system for evaluating the effects of a therapeutic on a brain of a patient in accordance with an aspect of the present invention.

FIG. 2 illustrates one example of a method for evaluating the effects of a therapeutic on a brain of a patient.

DETAILED DESCRIPTION

Figure 3:
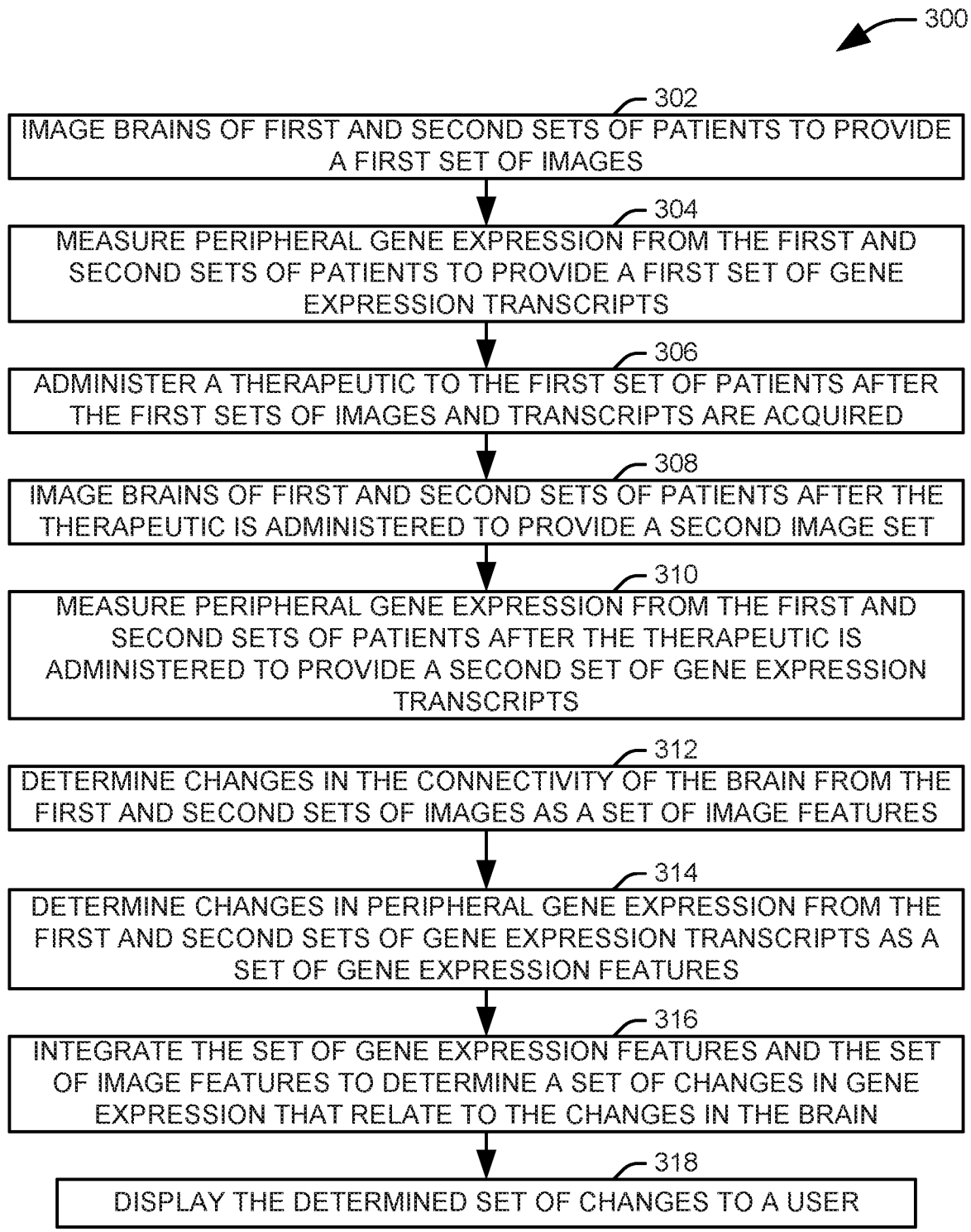
FIG. 3 illustrates an example of a method for evaluating the effects of a therapeutic on the functional connectome of a brain of a patient.

Systems and methods are provided for integrating changes in imaging with gene expression in blood or tissue cells. Various forms of imaging can be used to determine functional, structural, and neurochemical changes in the brain, and a measure of the gene expression can be integrated with the imaging to determine a molecular signature of the effect of the therapeutic on the brain. This molecular signature can then be verified in basic science studies and can be used to develop therapeutics. In one implementation, a joint independent component analysis (ICA) process is used to determine changes in the brain imaging that correlate with the changes in gene expression to determine the effects of the therapeutic.

As used herein, a "patient" can be a human or animal that is receiving medical or psychological treatment or the subject of a clinical study. A "therapeutic" can be any appropriate substance that would be expected to have a beneficial effect on the structure, function, or chemistry of a patient's brain. The terms "integrate" or "integrative analysis" each refer to the simultaneous statistical analysis of data from multiple platforms. The term "correlate" or "correlating," as used herein refers to any statistical process used to establish a mutual relationship among parameters and should not be read as limited to any specific means of determining such a mutual relationship unless otherwise stated. Two parameters are "correlated" when such a mutual relationship exists. Further, absolute simultaneity of two events is not required for both to occur "at a first time" or "at the same time," with two events occurring at a same time if they occur within a window of time in which significant changes in a measured value are unlikely to have occurred.

FIG. 1 illustrates one example of a system 100 for evaluating the effects of a therapeutic on a brain of a patient. It will be appreciated that the system 100 can be implemented as dedicated hardware, software instructions stored on a non-transitory medium and executed by an associated processor, or a combination of hardware and software. An imager interface 102 receives images of the brains of each of a first set of patients and a second set of patients using an appropriate imaging modality taken at a first time to provide a first set of images. The appropriate modality will vary with the application, but can include magnetic resonance imaging (MRI), computed axial tomography, functional MRI, diffuse tensor imaging, single photon emission computed tomography, positron emission tomography, and magnetic resonance spectroscopy. Similarly, an assay interface 104 receives data representing gene expression of each of the first set of patients and the second set of patients, measured, via blood or tissue, for example, skin tissue, withdrawn from the patient at the first time, to provide a first set of gene expression transcripts. A therapeutic can be administered to the first set of patients at a second time that is after the first time.

After the therapeutic is administered, the imager interface 102 receives images of the brains of each of the first set of patients and the second set of patients taken at a third time to provide a second set of images. Similarly, the assay interface 104 receives data representing a gene expression for each of the first set of patients and the second set of patients, measured, via blood or tissue withdrawn from the patient at the third time, to provide a second set of gene expression transcripts.

Each of the first set of images and the second set of images are provided to an image feature extractor 106 that determines, from the first set of images and the second set of images, a set of image features representing a functional, structural, or chemical change in the brain for each patient. The image feature extractor 106 can generate, for example, a difference image from the two images for each patient. Alternatively, a feature set can be extracted from each image, for example, representing volumetric measurements, levels of activity, or neurochemical concentrations associated with various brain structures and the two feature sets can be differenced to represent the change at the brain.

A gene expression feature extractor 108 determines, from the first set of gene expression transcripts and the second set of gene expression transcripts, a set of gene expression features representing a change in the gene expression for each patient. As with the image feature extractor 106, the gene expression feature extractor 108 can extract a plurality of features from each transcript, representing, for example, differences in expression values for one or more biological pathways of interest. Alternatively, differences can be calculated for all of the expression values for each patient as well as mean values across all patients, and only those pathways providing a significant change in the mean value between the first time and the third time are retained in the set of gene expression features. This analysis can be performed separately between the first set of patients and the second set of patients, with only significant changes unique to the first set of patients being retained as part of the set of gene expression features.

A therapeutic effect filter 110 integrates data from the set of image features and the set of gene expression features to determine a set of changes in the patient's gene expression that are related to changes in the structure, function, or chemistry of the brain. In one implementation, a correlation coefficient, such as a Pearson's correlation coefficient, is generated for each gene expression feature using multivariate regression over the image features. In another implementation, a Farrar-Glauber test is applied to identify correlated variables. In still another implementation, a parallel feature reduction process, such as joint independent component analysis, is applied to determine correlations between the two feature sets. The effects found to relate to with changes within the brain are then displayed to a user via a user interface 112.

The systems and methods presented herein were applied to investigate the effects of lithium on structural and functional brain imaging measures. Furthermore, a method to identify molecular pathways involved in lithium action was tested by integrating changes in brain imaging measures and peripheral gene expression to identify, in vivo, the molecular pathways involved in lithium action. A high-resolution structural scan and a functional resting scan was obtained using established methods, for example, the methods described in Altinay M., Karne, H., and Anand A., *Lithium Monotherapy Associated Clininal Improvement Effects on Amygdala-Ventromedial Prefrontal Cortex Resting State Connectivity in Bipolar Disorder. Journal of Affective Disorders*, 225: 4-12 (2018). (hereinafter "Anand 2018"). The entirety of the Anand 2018 publication is hereby incorporated by reference.

For structural data, voxel-based methodology (VBM) analysis was done, and the resultant grey matter (GM) images from the segmented images normalized to a standard MNI (Montreal Neurological Institute) space and smoothed with a ten-millimeter kernel. The difference between the images at two time points were created as a difference image. For functional data, the study focused on amygdala functional connectivity. Left & right amygdalas were used as regions of interest (ROIs), with whole brain voxel-wise correlation maps were generated using statistical parametric mapping separately for each ROI, which were then z-transformed and smoothed with an eight-millimeter kernel. The difference between the images at two time points were created as a difference image.

The study investigated both individual transcript gene expression as well as gene expression pathways (See Anand 2016). The expression values for each subject from an affymetrix gene chip was standardized across each gene. The average of the genes in the pathway were then calculated. The difference in the standardized values is then used as input in the gene modality of the fusion analysis. Lithium monotherapy was associated with changes within various resting state networks and in particular the task-positive network (p=0.05 corrected) and changes in the peripheral gene expression pathways (p=0.05). Changes in the functional connectome mediated the relationship between changes in gene expression and behavioral changes—multivariate regression analysis revealed significant correlation between fusion analysis imaging and gene components and changes in the Clinical Global Impression Scale (CGIS) for Bipolar Severity (p=0.05).

In view of the foregoing structural and functional features described above, methods in accordance with various aspects of the present invention will be better appreciated with reference to FIGS. 2 and 3. While, for purposes of simplicity of explanation, the methods of FIGS. 2 and 3 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement methods in accordance with an aspect the present invention.

FIG. 2 illustrates one example of a method 200 for evaluating the effects of a therapeutic on a brain of a patient. At 202, the brains of a first set of patients and a second set of patients are imaged at a first time to provide a first set of images. In the illustrated example, the first set of patients represent an experimental group for the therapeutic, while the second set of patients represent a control set. In practice, the imaging modality can be selected according to a type of change in the brain for which the therapeutic is to be evaluated. For example, to evaluate structural changes in the brain, such as the volume of brain regions, the thickness and surface area of brain regions, or changes in the structure of white matter fibers, a modality such as computed axial tomography (CAT) or magnetic resonance imaging (MRI) can be used. Diffuse tensor imaging techniques can be employed to evaluate microstructural changes in the brain and can be of particular value in quantifying changes in the structure of white matter fibers. Functional changes in the brain can be evaluated using functional MRI to evaluate task inducted activation or the resting state connectivity of the brain. Changes in brain chemistry can be determined using positron emission tomography or magnetic resonance spectroscopy.

At 204, a gene expression is measured in either blood cells or tissue stem cells, such as skin fibroblasts, for each of the first set of patients and the second set of patients. This can be done at the same time as the imaging to provide a first set of gene expression transcripts corresponding to the first set of images. At 206, a therapeutic is provided to the first set of patients at a second time that is after the first time. At 208, the brains of the first set of patients and the second set of patients are images at a third time, after the therapeutic is administered, to provide a second set of images. A 210, the gene expression of each of the first set of patients and the second set of patients at the third time to provide a second set of gene expression transcripts corresponding to the second set of images. It will be appreciated that sufficient time must pass between the introduction of the therapeutic and the measurements at 208 and 210 for meaningful changes in the function, structure, or chemistry of the brain and the patient's gene expression to be discernible. In one example, the third time is eight weeks after the administration of the therapeutic.

At 212, a change in one of the structure, function, and chemistry of the brain is determined for each of the first set of patients and the second set of patients from the first set of images and the second set of images. It will be appreciated that the manner in which this change is determined will vary with both the imaging modality and the change to the brain that is being evaluated. In one example, a voxel-wise correlation map of a region of interest within the brain can be generated via statistical parametric mapping to provide a set of features representing a change to the image. Examples of appropriate regions of interest can include a specific brain structure or portion thereof, such as the amygdala, the thalamus and/or the thalamic nuclei, the hypothalamus, the hippocampus, the putamen, the habenula, or a logical division of one of these structures (e.g., into left and right hemispheres), the lobes of the brain or a logical division of one of the lobes, the cerebral cortex and specific regions thereof, and regions comprising a specific tissue, such as gray matter or white matter. In another implementation, the set of changes are represented by difference image across the two images.

In another example, the change in the brain can be represented by a change across a plurality of imaging features. This change can be a difference between two images or a difference in respective measures of central tendency (e.g., arithmetic mean, geometric mean, or median) over groups of images taken either before or after introduction of the therapeutic. Examples of features can include a total volume of the brain, a volume of grey or white matter within the brain, a change in the volume or surface area of the putamen, the hippocampus, the thalamic nuclei, or the habenula, or a change in the volume of the frontal cortex, the parietal cortex, and the entire cortex. Other features can include the presence or concentration of various substances within the brain, as determined by PET imaging or magnetic resonance spectroscopy. Features representing the change in the brain can also be determined via various data reduction techniques such as principal component analysis, independent component analysis and cluster analysis.

At 214, the imaging features for each of the first set of patients and the second set of patients are integrated with the first and second sets of gene expression transcripts to determine a set of changes in the gene expression that are related with changes in the structure, function or chemistry of the brain. In one example, the imaging features and the changes in gene expression can be correlated across each of the first set of patients and the second set of patients to identify changes in the brain that are likely to be represent the effects of the administered therapeutic. Like the imaging features, the change at the gene expression transcripts can be represented as a number of extracted features, for example, representing changes in biological pathways in the assays. It will be appreciated that the specific pathways selected as features will vary with the type of cell assayed and the therapeutic administered. In one example, the features can include a change to a Glial-cell Derived Neurotrophic Factor family receptor pathway, a change to a Nuclear Activated T-Cells immune response pathway, and a change in a p53 signaling pathway. Data reduction techniques such as those described above can also be used to identify the gene expression components which change over treatment. In another implementation, joint independent component analysis between the changes in the images and the changes in the gene expression transcripts can be performed to determine the set of changes in the gene expression that are correlated with changes in the brain. Changes in the brain determined to be associated with the therapeutic can be displayed to a user at 216.

FIG. 3 illustrates an example of a method 300 for evaluating the effects of a therapeutic on the functional connectome of a brain of a patient. At 302, the brains of a first set of patients and a second set of patients are imaged at a first time to provide a first set of images. In the illustrated implementation, the imaging is intended to represent changes in the connectivity of the brain, and either or both of a functional imaging modality, such as fMRI or PET, and a structural imaging modality, such as computed tomography or MRI, is used. In the illustrated example, the brains of the patient are imaged via fMRI with the patient at rest. At 304, a peripheral gene expression is measured for each of the first set of patients and the second set of patients at the first time to provide a first set of gene expression transcripts. At 306, a therapeutic is administered to the first set of patients at a second time that is after the first time. In one example, the therapeutic is lithium.

At 308, the brains of the first set of patients and the second set of patients are images at a third time, after the therapeutic is administered, to provide a second set of images. A 310, the peripheral gene expression of each of the first set of patients and the second set of patients at the third time to provide a second set of gene expression transcripts corresponding to the second set of images. As noted previously, sufficient time must pass between the introduction of the therapeutic and the measurements at 308 and 310 for meaningful changes in the function, structure, or chemistry of the brain and the patient's gene expression to be discernible.

At 312, a change in the connectivity of the brain for each of the first set of patients and the second set of patients is determined from the first set of images and the second set of images. In one implementation, a difference image is generated from the images for each patient. At 314, a set of changes in peripheral gene expression is determined. In one example, the peripheral gene expression was conducted by including RNA transcripts which showed a difference before and after treatment were included for pathway analysis, and biological pathways showing significant differences were included in the analysis. A composite score for each pathway was calculated from the mean of treatment related difference in each of the transcripts present in the pathway.

At 316, the change in the connectivity of the brain is integrated with the set of changes in peripheral gene expression to determine a set of changes in the peripheral gene expression that are related to changes in the functional connectome of the brain. In one implementation, the difference image and the set of changes in peripheral gene expression using parallel independent component analysis (ICA). In one example, a repeated measures ANOVA can be used in combination with the parallel ICA to control for the effects of state. Once the set of changes in the peripheral gene expression that are related to changes in the connectivity of the brain is determined, it is displayed to a user at an associated display at 318.

Figure 4:
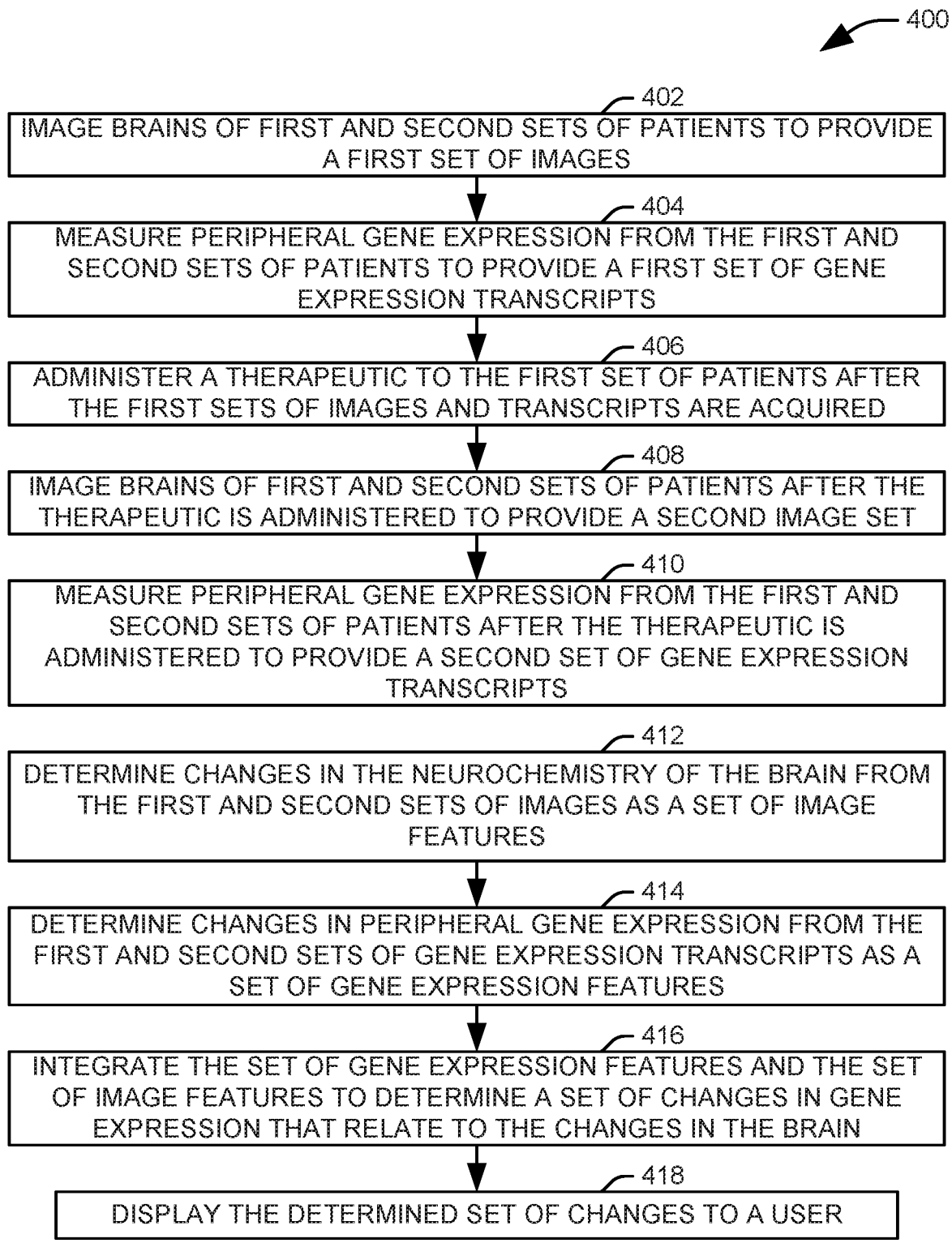
FIG. 4 illustrates an example of a method for evaluating the effects of a therapeutic on the neurochemistry of a brain of a patient.

FIG. 4 illustrates an example of a method 400 for evaluating the effects of a therapeutic on the neurochemistry of a brain of a patient. At 402, the brains of a first set of patients and a second set of patients are imaged at a first time to provide a first set of images. In the illustrated implementation, the imaging is intended to represent changes in the neurochemistry of the brain, and a functional imaging modality is used, such as fMRI or PET. In the illustrated example, the brains of the patient are imaged via fMRI with the patient at rest. At 404, a peripheral gene expression is measured for each of the first set of patients and the second set of patients at the first time to provide a first set of gene expression transcripts. At 406, a therapeutic is administered to the first set of patients at a second time that is after the first time. In one example, the therapeutic is lithium.

At 408, the brains of the first set of patients and the second set of patients are images at a third time, after the therapeutic is administered, to provide a second set of images. A 410, the peripheral gene expression of each of the first set of patients and the second set of patients at the third time to provide a second set of gene expression transcripts corresponding to the second set of images. As noted previously, sufficient time must pass between the introduction of the therapeutic and the measurements at 408 and 410 for meaningful changes in chemistry of the brain and the patient's gene expression to be discernible.

At 412, a change in the neurochemistry of the brain for each of the first set of patients and the second set of patients is determined from the first set of images and the second set of images. In one implementation, a difference image is generated from the images for each patient. At 414, a set of changes in peripheral gene expression is determined. In one example, the peripheral gene expression was conducted by including RNA transcripts which showed a difference before and after treatment were included for pathway analysis, and biological pathways showing significant differences were included in the analysis. A composite score for each pathway was calculated from the mean of treatment related difference in each of the transcripts present in the pathway.

At 416, the change in the neurochemistry of the brain is integrated with the set of changes in peripheral gene expression to determine a set of changes in the peripheral gene expression that are related to chemistry of the brain. In one implementation, the difference image and the set of changes in peripheral gene expression using parallel independent component analysis (ICA). In one example, a repeated measures ANOVA can be used in combination with the parallel ICA to control for the effects of state. Once the set of changes in the peripheral gene expression that are related to changes in the neurochemistry of the brain is determined, it is displayed to a user at an associated display at 418.

Figure 5:
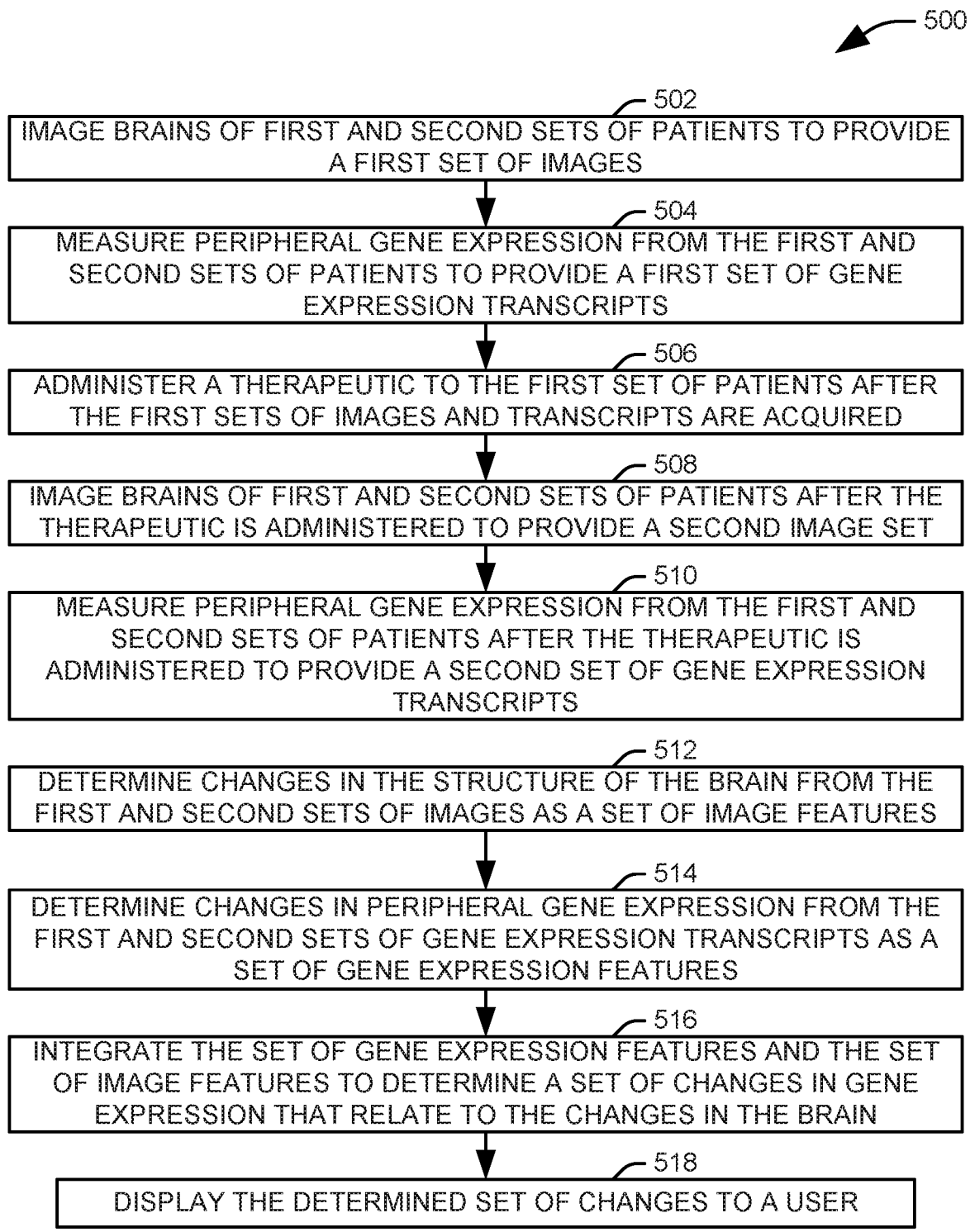
FIG. 5 illustrates an example of a method for evaluating the effects of a therapeutic on the structure of a brain of a patient.

FIG. 5 illustrates an example of a method 500 for evaluating the effects of a therapeutic on the structure of a brain of a patient. At 502, the brains of a first set of patients and a second set of patients are imaged at a first time to provide a first set of images. In the illustrated implementation, the imaging is intended to represent changes in the structure of the brain, and a structural imaging modality, such as computed tomography or MRI, is used. In the illustrated example, the brains of the patient are imaged via MRI. At 504, a peripheral gene expression is measured for each of the first set of patients and the second set of patients at the first time to provide a first set of gene expression transcripts. At 506, a therapeutic is administered to the first set of patients at a second time that is after the first time. In one example, the therapeutic is lithium.

At 508, the brains of the first set of patients and the second set of patients are images at a third time, after the therapeutic is administered, to provide a second set of images. A 510, the peripheral gene expression of each of the first set of patients and the second set of patients at the third time to provide a second set of gene expression transcripts corresponding to the second set of images. As noted previously, sufficient time must pass between the introduction of the therapeutic and the measurements at 508 and 510 for meaningful changes in the structure of the brain and the patient's gene expression to be discernible.

At 512, a change in the structure of the brain for each of the first set of patients and the second set of patients is determined from the first set of images and the second set of images. In one implementation, a difference image is generated from the images for each patient. At 514, a set of changes in peripheral gene expression is determined. In one example, the peripheral gene expression was conducted by including RNA transcripts which showed a difference before and after treatment were included for pathway analysis, and biological pathways showing significant differences were included in the analysis. A composite score for each pathway was calculated from the mean of treatment related difference in each of the transcripts present in the pathway.

At 516, the change in the structure of the brain is integrated with the set of changes in peripheral gene expression to determine a set of changes in the peripheral gene expression that are related to changes in the structure of the brain. In one implementation, the difference image and the set of changes in peripheral gene expression using parallel independent component analysis (ICA). In one example, a repeated measures ANOVA can be used in combination with the parallel ICA to control for the effects of state. Once the set of changes in the peripheral gene expression that are related to changes in the structure of the brain is determined, it is displayed to a user at an associated display at 518.

Figure 6:
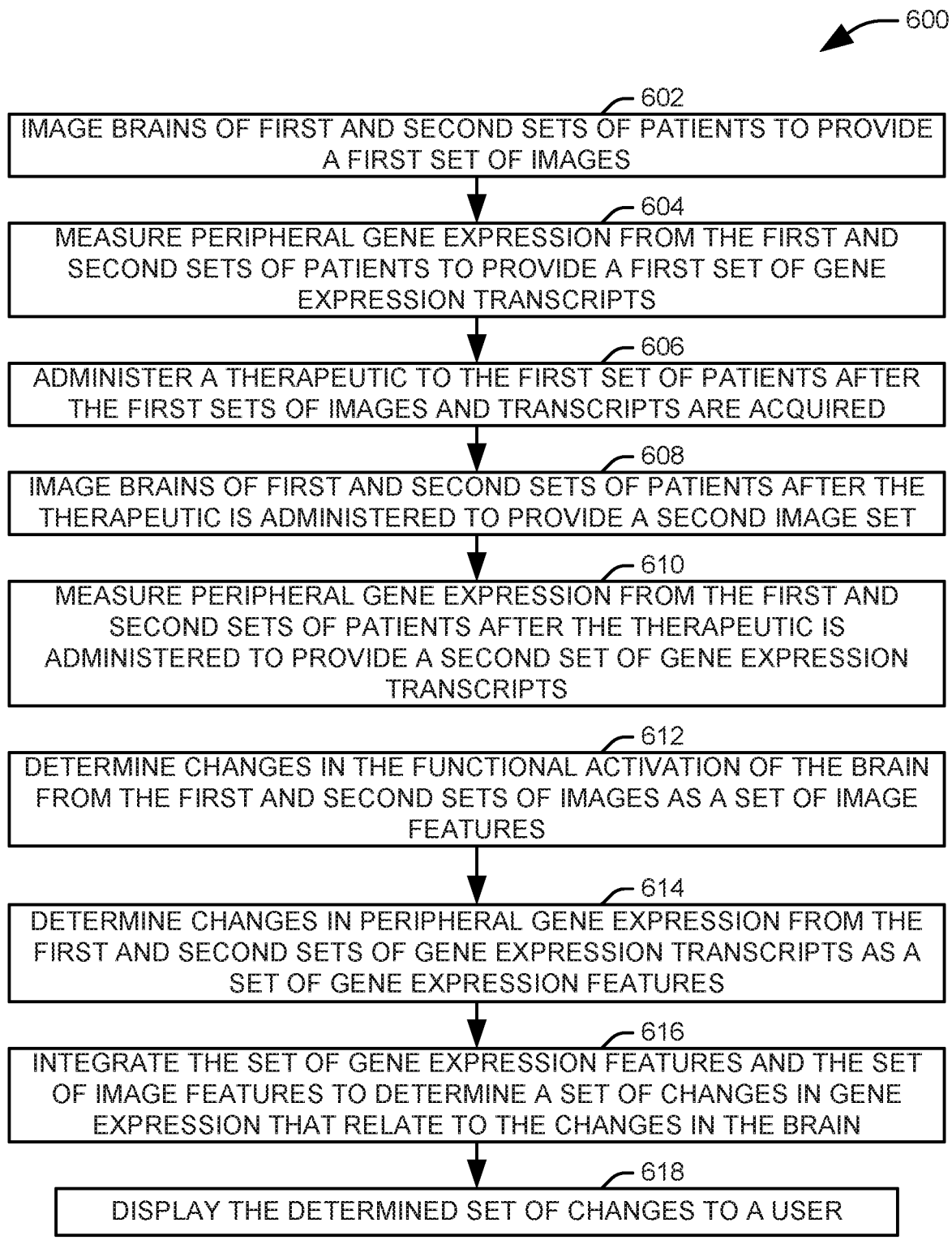
FIG. 6 illustrates an example of a method for evaluating the effects of a therapeutic on the functional activation of a brain of a patient.

FIG. 6 illustrates an example of a method 600 for evaluating the effects of a therapeutic on the functional activation of a brain of a patient. At 602, the brains of a first set of patients and a second set of patients are imaged at a first time to provide a first set of images. In the illustrated implementation, the imaging is intended to represent changes in the functional activation of the brain, and a functional imaging modality is used, such as fMRI or PET. In the illustrated example, the brains of the patient are imaged via fMRI with the patient at rest. At 604, a peripheral gene expression is measured for each of the first set of patients and the second set of patients at the first time to provide a first set of gene expression transcripts. At 606, a therapeutic is administered to the first set of patients at a second time that is after the first time. In one example, the therapeutic is lithium.

At 608, the brains of the first set of patients and the second set of patients are images at a third time, after the therapeutic is administered, to provide a second set of images. A 610, the peripheral gene expression of each of the first set of patients and the second set of patients at the third time to provide a second set of gene expression transcripts corresponding to the second set of images. As noted previously, sufficient time must pass between the introduction of the therapeutic and the measurements at 608 and 610 for meaningful changes in functional activation of the brain and the patient's gene expression to be discernible.

At 612, a change in the functional activation of the brain for each of the first set of patients and the second set of patients is determined from the first set of images and the second set of images. In one implementation, a difference image is generated from the images for each patient. At 614, a set of changes in peripheral gene expression is determined. In one example, the peripheral gene expression was conducted by including RNA transcripts which showed a difference before and after treatment were included for pathway analysis, and biological pathways showing significant differences were included in the analysis. A composite score for each pathway was calculated from the mean of treatment related difference in each of the transcripts present in the pathway.

At 616, the change in the functional activation of the brain is integrated with the set of changes in peripheral gene expression to determine a set of changes in the peripheral gene expression that are related to function of the brain. In one implementation, the difference image and the set of changes in peripheral gene expression using parallel independent component analysis (ICA). In one example, a repeated measures ANOVA can be used in combination with the parallel ICA to control for the effects of state. Once the set of changes in the peripheral gene expression that are related to changes in the functional activation of the brain is determined, it is displayed to a user at an associated display at 618.

Figure 7:
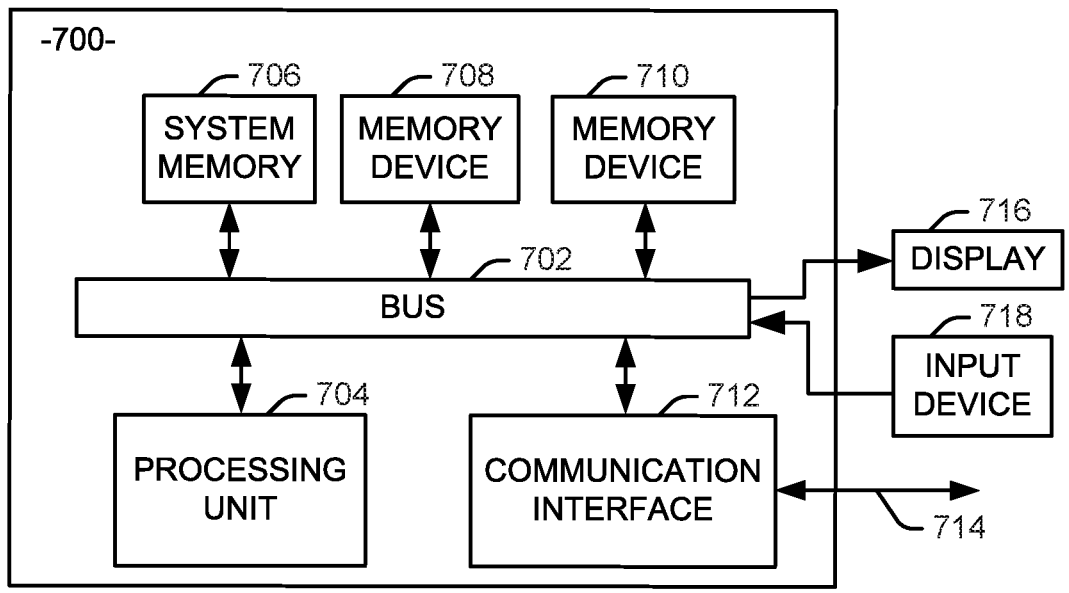
FIG. 7 is a schematic block diagram illustrating an exemplary system of hardware components capable of implementing examples of the systems and methods disclosed in FIGS. 1-6.

FIG. 7 is a schematic block diagram illustrating an exemplary system 700 of hardware components capable of implementing examples of the systems and methods disclosed in FIGS. 1-6. The system 700 can include various systems and subsystems. The system 700 can be a personal computer, a laptop computer, a workstation, a computer system, an appliance, an application-specific integrated circuit (ASIC), a server, a server blade center, a server farm, etc.

The system 700 can includes a system bus 702, a processing unit 704, a system memory 706, memory devices 708 and 710, a communication interface 712 (e.g., a network interface), a communication link 714, a display 716 (e.g., a video screen), and an input device 718 (e.g., a keyboard and/or a mouse). The system bus 702 can be in communication with the processing unit 704 and the system memory 706. The additional memory devices 708 and 710, such as a hard disk drive, server, stand-alone database, or other non-volatile memory, can also be in communication with the system bus 702. The system bus 702 interconnects the processing unit 704, the memory devices 706-710, the communication interface 712, the display 716, and the input device 718. In some examples, the system bus 702 also interconnects an additional port (not shown), such as a universal serial bus (USB) port.

The processing unit 704 can be a computing device and can include an application-specific integrated circuit (ASIC). The processing unit 704 executes a set of instructions to implement the operations of examples disclosed herein. The processing unit can include a processing core. The additional memory devices 706, 708, and 710 can store data, programs, instructions, database queries in text or compiled form, and any other information that can be needed to operate a computer. The memories 706, 708, and 710 can be implemented as computer-readable media (integrated or removable) such as a memory card, disk drive, compact disk (CD), or server accessible over a network. In certain examples, the memories 706, 708, and 710 can comprise text, images, video, and/or audio, portions of which can be available in formats comprehensible to human beings. Additionally or alternatively, the system 700 can access an external data source or query source through the communication interface 712, which can communicate with the system bus 702 and the communication link 714.

In operation, the system 700 can be used to implement one or more parts of a system in accordance with the present invention, such as that described in FIG. 1. Computer executable logic for implementing the various functional components of the system resides on one or more of the system memory 706, and the memory devices 708, 710 in accordance with certain examples. The processing unit 704 executes one or more computer executable instructions originating from the system memory 706 and the memory devices 708 and 710. The term "computer readable medium" as used herein refers to a medium that participates in providing instructions to the processing unit 704 for execution.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

In the preceding description, specific details have been set forth in order to provide a thorough understanding of example implementations of the invention described in the disclosure. However, it will be apparent that various implementations may be practiced without these specific details. For example, circuits, systems, networks, processes, and other components may be shown as components in block diagram form in order not to obscure the example implementations in unnecessary detail. In other instances, well-known circuits, processes, algorithms, structures, and techniques may be shown without unnecessary detail in order to avoid obscuring the examples. The description of the example implementations will provide those skilled in the art with an enabling description for implementing an example of the invention, but it should be understood that various changes may be made in the function and arrangement of elements without departing from the spirit and scope of the invention. Accordingly, the present invention is intended to embrace all such alterations, modifications, and variations that fall within the scope of the appended claims.

What is claimed is:

1. A method comprising:
   imaging the brains of each of a set of patients at a first imaging system having an associated imaging modality at a first time to provide a first set of images;
   measuring a gene expression in one of blood cells and tissue stem cells of each of the set of patients at the first time to provide a first set of gene expression transcripts;
   administering a therapeutic to the set of patients after the first time;
   imaging the brains of each of the set of patients at one of the first imaging system and a second imaging system having the associated imaging modality at a second time that is after the administration of the therapeutic to provide a second set of images;
   measuring the gene expression of each of the set of patients at the second time to provide a second set of gene expression transcripts;

determining, from the first set of images and the second set of images, a change in one of the structure, function, and chemistry of the brain for each of the set of patients;

determining, from the first set of gene expression transcripts and the second set of gene expression transcripts, a change in gene expression for each of the set of patients; and correlating the change in the one of the structure, function, and chemistry of the brain for each of the set of patients, with the change in gene expression across the set of patients to determine a set of changes in the gene expression that are related to changes in the structure, function or chemistry of the brain, the set of changes in the gene expression representing the changes in gene expression that are attributable to the therapeutic;

applying the therapeutic to a patient having a given disorder based on the set of changes in gene expression.

2. A system comprising:

an imaging system;

an output device;

a processor; and a non-transitory computer readable medium that stores executable instructions, the executable instructions comprising:

an imager interface that receives, from the imaging system, a first set of images representing brains of a set of patients at a first time and a second set of images representing the brains of the set of patients at a second time that is after administration of a therapeutic to provide a second set of images;

an assay interface that receives a first set of gene expression transcripts measuring a gene expression of each of the set of patients at the first time and a second set of gene expression transcripts measuring a gene expression of each of the set of patients at the second time;

an image feature extractor that determines, from the first set of images and the second set of images, a set of image features representing a functional, structural, or chemical change in the brain for each patient;

a gene expression feature extractor determines, from the first set of gene expression transcripts and the second set of gene expression transcripts, a set of gene expression features representing a change in the gene expression for each patient of the set of patients; and a therapeutic effect filter that determines, via correlation of the set of image features and the set of gene expression features across the set of patients, a set of changes in the gene expression that are related to changes in the connectivity of the brain and that are attributable to the therapeutic; and a user interface that displays a molecular signature for the therapeutic, derived from the set of changes in the gene expression that are related to changes in the connectivity of the brain and representing the effect of the therapeutic on the brain, at the output device.

3. A method comprising:

imaging the brains of a set of patients at a first imaging system having an associated imaging modality at a first time to provide a first set of images;

measuring a peripheral lymphocyte gene expression of the set of patients at the first time to provide a first set of gene expression transcripts;

imaging the brains of the set of patients at one of the first imaging system and a second imaging system having the associated imaging modality at a second time to provide a second set of images;

measuring the peripheral lymphocyte gene expression of the set of patients at the second time to provide a second set of gene expression transcripts;

administering a therapeutic to the set of patients at a third time between the first time and the second time;

determining, from the first set of images and the second set of images, a change in the connectivity of the brain for the set of patients;

determining, from the first set of gene expression transcripts and the second set of gene expression transcripts, a change in gene expression for each of the set of patients; and determining, from the change in the connectivity of the brain for the set of patients, the change in gene expression for each of the set of patients, a set of changes in the peripheral lymphocyte gene expression that are correlated with changes in the connectivity of the brain, the set of changes in the peripheral lymphocyte gene expression representing the changes in gene expression that are attributable to the therapeutic;

applying the therapeutic to a patient having a given disorder based on the set of changes in gene expression.

4. The method of claim 1, wherein imaging the brains of each of the first set of patients and the second set of patients at the first time comprises imaging the brains via a functional imaging modality.

5. The method of claim 4, wherein imaging the brains of each of the first set of patients and the second set of patients at the first time comprises imaging the brains via functional magnetic resonance imaging.

6. The method of claim 1, wherein integrating the change in the one of the structure, function, and chemistry of the brain for each of the first set of patients and the second set of patients, the first set of gene expression transcripts, and the second set of gene expression transcripts comprises generating a voxel-wise correlation map of a region of interest within the brain via statistical parametric mapping.

7. The method of claim 6, wherein the region of interest of the brain includes at least one of the left amygdala and the right amygdala of the brain.

8. The method of claim 1, wherein integrating the change in the one of the structure, function, and chemistry of the brain for each of the first set of patients and the second set of patients, the first set of gene expression transcripts, and the second set of gene expression transcripts comprises generating a plurality of imaging features for each of the first set of patients and the second set of patients from the first and second sets of images and generating a correlation coefficient between each of a plurality of imaging features across the first set of patients and the second set of patients and each change in the peripheral lymphocyte gene expression in a set of changes in the peripheral lymphocyte gene expression.

9. The method of claim 8, wherein the plurality of imaging features include a total volume of the brain and a volume of grey matter within the brain.

10. The method of claim 8, wherein the set of changes in the peripheral lymphocyte gene expression includes at least one of a change to a Glial-cell Derived Neurotrophic Factor family receptor pathway, a change to a Nuclear Activated T-Cells immune response pathway, and a change in a p53 signaling pathway.

11. The method of claim 8, wherein the plurality of imaging features include a change in the volume of at least one of the putamen, the hippocampus, the thalamic nuclei, and the habenula.

12. The method of claim 8, wherein the plurality of imaging features include a change in the volume of at least one of the frontal cortex, the parietal cortex, and the entire cortex.

13. The method of claim 1, wherein integrating the change in the one of the structure, function, and chemistry of the brain for each of the first set of patients and the second set of patients, the first set of gene expression transcripts, and the second set of gene expression transcripts comprises generating a difference image for each of the first set of patients and the second set of patients from the first and second sets of images and applying joint independent component analysis to the difference images and a set of changes in the peripheral lymphocyte gene expression for each of the first set of patients and the second set of patients.

14. The method of claim 1, wherein the one of the structure, function, and chemistry of the brain is a functional activation of the brain.

15. The method of claim 1, wherein the one of the structure, function, and chemistry of the brain is a neurochemistry of the brain.

16. The method of claim 1, wherein the one of the structure, function, and chemistry of the brain is a structure of the brain.

17. The system of claim 2, wherein the first set of images and the second set of images are functional magnetic resonance (fMRI) images.

18. The system of claim 2, wherein the therapeutic effect filter applies joint independent component analysis to the set of image features and the set of gene expression features to determine the set of changes in the gene expression that are correlated with changes in the connectivity of the brain and that are attributable to the therapeutic.

19. The system of claim 18, wherein the image feature extractor generates a set of difference images from the first set of images and the second set of images as the set of image features.

20. The system of claim 2, wherein the image feature extractor generates a voxel-wise correlation map between the first set of images and the second set of images for a region of interest within the brain via statistical parametric mapping.

* * * * *